United States Patent [19]

Hasegawa et al.

[11] Patent Number: 4,504,583
[45] Date of Patent: Mar. 12, 1985

[54] PROCESS FOR CRYSTALLIZING EGG WHITE LYSOZYME

[75] Inventors: Mineo Hasegawa, Hachioji; Kazuya Yoshida, Fuchu; Sakae Miyauchi, Saitama; Masami Terazono, Goka, all of Japan

[73] Assignee: Kewpie Kabushiki Kaisha, Tokyo, Japan

[21] Appl. No.: 445,715

[22] Filed: Nov. 30, 1982

[30] Foreign Application Priority Data

Jun. 2, 1982 [JP] Japan .............................. 57/94455

[51] Int. Cl.³ .............................................. C12N 9/36
[52] U.S. Cl. ................................ 435/206; 435/814; 435/815; 435/816; 426/32
[58] Field of Search ............ 426/32; 435/206, 814, 435/815, 816

[56] References Cited

U.S. PATENT DOCUMENTS

| | | | |
|---|---|---|---|
| 2,579,455 | 12/1951 | Alderton et al. | 435/206 |
| 3,419,471 | 12/1968 | Matsuoka et al. | 435/206 |
| 3,513,074 | 5/1970 | Matsuoka et al. | 435/206 |
| 3,515,643 | 6/1970 | Ghielmetti et al. | 435/206 |
| 3,586,607 | 6/1971 | Notarianni et al. | 435/206 |
| 3,627,642 | 12/1971 | Suyama et al. | 435/206 |

OTHER PUBLICATIONS

*Chemical Abstracts*, vol. 94 (15), Abstract No. 116352m, Morozov, V. N. et al., "Viscoelastic properties of protein crystals: triclinic crystals of hen egg white lysozyme in different conditions".
*Chemical Abstracts*, vol. 70 (19), Abstract No. 84490r, Cole, J. B. et al., "Thermodynamics of solution of lysozyme crystals".
*Chemical Abstracts*, vol. 72 (25), Abstract No. 128984c, LaRue, J. N. et al., "Turkey egg white lysozyme. Preparation of the crystalline enzyme and investigation of the amino acid sequence".
Karger, B. L. et al., *An Introduction to Separation Science*, John Wiley and Sons, New York, pp. 312–313 (1973).

*Primary Examiner*—Robert J. Warden
*Assistant Examiner*—Jayme A. Huleatt
*Attorney, Agent, or Firm*—Oblon, Fisher, Spivak, McClelland & Maier

[57] ABSTRACT

In the process of crystallizing egg white lysozyme by cooling a salt solution containing egg white lysozyme, a seed crystal is added to the solution, which solution is then maintained at a temperature of about 10° C. to 28° C. for a certain period of time and subsequently cooled, whereby lysozyme can be crystallized to form an agglomerate of many individual needle crystals. The solution containing crystalline lysozyme thus obtained can be filtered within an extremely short period of time, that is, within only a few minutes.

9 Claims, No Drawings

PROCESS FOR CRYSTALLIZING EGG WHITE LYSOZYME

BACKGROUND OF THE INVENTION

The present invention relates generally to a process for crystallizing egg white lysozyme, and more particularly to a process for crystallizing egg white lysozyme by which crystallized egg white lysozyme can be collected more rapidly than heretofore.

Heretofore, the so-called "crude lysozyme" extracted from egg white by adsorption or salting out has been purified ordinarily by adjusting the pH of an aqueous sodium chloride solution containing the crude lysozyme dissolved therein to a value of the order of 9.5 so that crystalline lysozyme will be formed by isoelectric precipitation. Ordinarily, in this process, the aqueous sodium chloride solution is cooled to a temperature of the order of 0° C. to 5° C. and then a small quantity of a seed crystal is added, or a small quantity of a seed crystal is added and immediately thereafter the solution is cooled to a temperature of the same order thereby to facilitate the formation of crystalline lysozyme.

However, when 1 liter, for example, of an aqueous sodium chloride solution opacified or clouded with crystallized lysozyme obtained after about 10 hours of crystallization in accordance with the process described above is filtered through Toyo Filter Paper No. 2 having a filter area of 300 cm$^2$ under a gauge pressure of 1.5 kg/cm$^2$ to collect the lysozyme crystals, more than 20 minutes are required for the filtration presumably because the filter paper clogs. Thus, this crystallization process is accompanied by the problem of an excessively long period of time required for the subsequent filtration operation.

We have continued extensive research in order not only to solve this problem encountered in the purification of crude lysozyme mentioned above but also to overcome a similar problem encountered in the crystallization of lysozyme by a salt concentration adjustment from a common salt solution containing lysozyme dissolved therein, such as an eluate obtained by eluting lysozyme adsorbed on any type of resin in accordance with the conventional adsorption method. That is, an object of our study was to provide a novel process for crystallizing lysozyme by which crystallized lysozyme can be collected more rapidly or, more particularly, by which filtration can be simplified.

As a result, it has been found that, by adding a seed crystal to a salt solution containing lysozyme, maintaining the solution at about 10° C. to 28° C. for a certain period of time, and then cooling the resulting solution, the subsequent filtration operation can be completed within an extremely short period of time, that is, within only a few minutes.

SUMMARY OF THE INVENTION

An object of the present invention is to provide a process for crystallizing egg white lysozyme by which crystallized lysozyme can be collected at a fast rate on the basis of the above finding.

The present invention which has achieved this object provides a process for crystallizing egg white lysozyme by cooling a salt solution containing egg white lysozyme which comprises adding a seed crystal to the solution, maintaining the solution at a temperature of about 10° C. to 28° C. for a certain period of time, and then cooling the resulting solution.

DETAILED DESCRIPTION OF THE INVENTION

The term "salt solution containing egg white lysozyme" as used herein is intended to mean an aqueous solution of, for example, a sodium, potassium or ammonium salt, a buffer solution obtained by admixing any of these salts with an aqueous solution of an acid or an alkali having either one of the ions (anion or cation) constituting the salt, or like solution, which aqueous solution contains a certain quantity, e.g., 1 to 50 g/l, of egg white lysozyme dissolved therein. The salt concentration of the salt solution is maintained at a level applicable, for example, to the salting out of lysozyme, and ordinarily is of the order of 3 to 5% by weight. Examples of such salt solutions are an aqueous sodium chloride solution containing a certain quantity of crude lysozyme dissolved therein to be purified and a salt eluate obtained by eluting lysozyme adsorbed on an type of weakly acidic cation exchange resin.

In accordance with the present invention, a seed crystal is added to the salt solution containing egg white lysozyme as defined above, and the solution is then maintained at a temperature of about 10° C. to 28° C. for a certain period of time. Prior to the addition of the seed crystal, the pH of the salt solution is adjusted ordinarily to about 9.5 by a conventional method generally with 0.5 to 1.0N caustic soda.

For the seed crystal, a separately prepared isoelectric suspension of 1 to 10% crystalline lysozyme in a 5% aqueous solution of NaCl or KCl, for instance, is used. This seed crystal is added to the salt solution in a proportion of about 3 to 50 mg as crystalline lysozyme per liter of the solution in the same manner as in the conventional process.

This solution is then maintained at a temperature of about 10° C. to 28° C., preferably 15° C. to 25° C., for certain period of time with stirring at a very low speed preferably at a speed of about 5 to 20 r.p.m. As will be apparent from the data on the Examples of Experiment set forth hereinlater, it is difficult to shorten the filtration time when the solution is maintained at a temperature outside the above range. Further, the solution preferably maintained at the specified temperature for at least about 1 hour, generally about 1 to 3 hours, in order to shorten the filtration time effectively as will also be apparent from the same Examples. The solution thus maintained becomes slightly opaque or cloudy throughout.

The resulting solution is cooled to crystallize lysozyme. The cooling is effected generally at a temperature ranging from about 0° C. to 5° C. while the solution stirred at a speed of about 5 to 20 r.p.m. until the entire solution becomes considerably opaque or cloudy. Ordinarily, the crystallization can be completed about 8 to 10 hours after the addition of the seed crystal. Throughout the crystallization process of this invention, it desirable that the solution be stirred continually at speed sufficient to promote growth of lysozyme crystal and to prevent precipitation of crystals thus formed preferably at a speed as low as the range specified above.

The salt solution which has completed crystallization and become opacified or cloudy with lysozyme is then subjected to filtration. The filtration may be conducted in accordance with a conventional method. For i stance, 1 liter of a salt solution containing lysozyme crystals may be filtered through Toyo Filter Paper No. 2 having a filter area of 300 cm² under a gauge pressure of 1.5 kg/cm². The filtration conducted under these conditions can be completed ordinarily within 1 to 2 minutes. In the case where a filter cloth of about 200 mesh is used in lieu of the filter paper, the filtration can also be completed within about 1 minute. Moreover, even with a filter cloth, there is little likelihood of the crystals escaping therethrough, and for this reason there is no probability of a reduction in yield.

In accordance with the crystallization process of the present invention, about 1 liter of a salt solution containing lysozyme crystals can thus be filtered within only a few minutes, whereas more than 20 minutes were required in the conventional process. Although the reason for this is uncertain, the filtration can be completed within an extremely short period of time, i.e., only 1 to 2 minutes, presumably because the filter does not easily become clogged since needle crystals of lysozyme obtained by the crystallization process of the present invention, while having a size similar to that of the crystals collected by the conventional method, agglomerate to form something like a mass of entangled pine needles. These phenomena have been verified by the observation under the microscope. Although it is not clear why individual needle crystals can be entangled to form an agglomerate, a possible reason may be that the salt solution containing egg white lysozyme is not directly cooled to a temperature as low as 0° C. to 5° C., but is first maintained at 10° C. to 28° C. for a certain period of time and then cooled. Such an agglomerate seems to be formed effectively when the salt solution is continually stirred at a speed as low as 5 to 20 r.p.m. throughout the crystallization process as will be apparent from the data on the Examples of Experiment described hereinlater.

The following data obtained by experimentation will show how easily the filtration can be performed in accordance with the crystallization process of this invention in comparison with the conventional process.

EXAMPLE OF EXPERIMENT 1

To 1 liter of a 3% aqueous sodium chloride solution containing 3 g of crude lysozyme dissolved therein and adjusted to a pH of 9.5 with 1N caustic soda was added 0.4 g of a separately prepared isoelectric suspension of 5% crystalline lysozyme in a 5% aqueous sodium chloride solution (about 20 mg of crystalline lysozyme as a seed crystal). The resulting solution was maintained at 20° C. for a certain period of time, and then cooled to around 2° C. The solution was further maintained at this temperature for a certain period of time until a total of these time periods reached 8 hours. Then the resultant opaque or cloudy solution was filtered through Toyo Filter Paper No. 2 having a filter area of 300 cm² under a gauge pressure of 1.5 kg/cm². Throughout the crystallization process, the solution was continually stirred at a speed of 10 r.p.m. with an agitator inserted in the solution.

The results obtained by measuring the time required for the filtration when the retention times at 20° C. were 0 hr., 0.5 hr., 1 hr., 2 hr., and 3 hr., respectively, in the crystallization process are set forth in Table 1.

TABLE 1

|  | Retention time at 20° C. (hr.) | Retention time at 2° C. (hr.) | Filtration time (min.) | Recovery of crystalline lysozyme (g) |
|---|---|---|---|---|
| Control | 0 | 8 | ca. 20 | 2.58 |
| Present Invention | 0.5 | 7.5 | ca. 9 | 2.62 |
|  | 1.0 | 7.0 | ca. 1 | 2.71 |
|  | 2.0 | 6.0 | ca. 1 | 2.75 |
|  | 3.0 | 5.0 | ca. 1 | 2.80 |

Note 1:
In the conventional process, similar results were obtained when the seed crystals were added after the solution had been cooled to 2° C.
Note 2:
In the process of the present invention, about 18 minutes were required for the filtration when the solution was maintained at 20° C. with relatively vigorous stirring at a speed of about 1,000 to 4,000 r.p.m. and then left standing at 2° C. in one case, and maintained at 2° C. with the same speed of stirring in the other case.

EXAMPLE OF EXPERIMENT 2

Lysozyme was crystallized by the procedure of Example of Experiment 1 except that an aqueous sodium chloride solution prepared in accordance with the procedure of Example of Experiment 1 and containing crude lysozyme together with seed crystals added thereto was maintained at a certain temperature for 2 hours and further maintained at around 2° C. for 6 hours. The lysozyme thus crystallized was subsequently filtered under the same conditions as in Example of Experiment 1.

The results obtained by measuring the time required for the filtration when the temperatures were 2° C., 6° C., 10° C., 15° C., 20° C., 25° C., 28° C., 30° C., and 35° C., respectively, in the crystallization process are summarized in Table 2.

TABLE 2

|  | Predetermined temperature (°C.) | Filtration time (min.) | Recovery of crystalline lysozyme (g) |
|---|---|---|---|
| Control | 2 | ca. 20 | 2.60 |
|  | 6 | ca. 15 | 2.62 |
| Present Invention | 10 | ca. 6 | 2.62 |
|  | 15 | ca. 1 | 2.81 |
|  | 20 | ca. 1 | 2.75 |
|  | 25 | ca. 2 | 2.63 |
|  | 28 | ca. 12 | 2.58 |
| Control | 30 | ca. 18 | 2.57 |
|  | 35 | ca. 20 | 2.55 |

In order to indicate more fully the nature and utility of this invention, the following specific examples of practice constituting preferred embodiments of the invention are set forth, it being understood that these examples are presented as illustrative only and are not intended to limit the scope of the invention.

EXAMPLE 1

Lysozyme was crystallized by the procedure of Example of Experiment 1 except that the solution was maintained at 20° C. for 1 hour and then at 4° C., instead of 2° C., for 7 hours.

The opaque solution obtained was filtered similarly as in Example of Experiment 1. The filtration was completed within about 1 minute, and 2.70 g of crystalline lysozyme was collected.

EXAMPLE 2

Lysozyme was collected by the procedure of Example of Experiment 2 except that the solution was maintained at 15° C. for 2 hours.

The opaque solution obtained was filtered through a filter cloth of 200 mesh under a gauge pressure of 1.5 kg/cm². The filtration was completed within about 1 minute, and 2.83 g of crystalline lysozyme was collected.

EXAMPLE 3

Lysozyme was crystallized by the procedure of Example 1 except that the solution containing crude lysozyme was replaced by 1,000 ml of an eluate obtained by eluting with a 5% aqueous sodium chloride solution a resin having lysozyme adsorbed thereon, which resin had been obtained by a conventional method from 1,000 ml of egg white and 200 ml of an ion exchange resin, Amberlite IRC-50 (supplied by Rohm & Haas Co.). The lysozyme thus crystallized was then filtered similarly as in Example 1. The filtration was completed within about 1 minute, and 2.94 g of crystalline lysozyme was collected.

EXAMPLE 4

Lysozyme was crystallized by the procedure of Example 3 except that the 5% aqueous sodium chloride solution and the isoelectric suspension of 5% crystalline lysozyme in a 5% aqueous sodium chloride solution used as a seed crystal were replaced respectively by a 5% aqueous potassium chloride solution and an isoelectric suspension of 3% crystalline lysozyme in a 5% aqueous potassium chloride solution. The lysozyme thus crystallized was then filtered similarly as in Example 3. The filtration was completed within about 1 minute, and 2.65 g of crystalline lysozyme was collected.

What we claim is:

1. A process for producing crystallized egg white lysozyme, comprising:
    (a) adding a seed crystal of crystalline lysozyme to a salt solution having egg white lysozyme dissolved therein;
    (b) allowing the salt solution to stand at a temperature of about 10° C. to 28° C. for at least about one hour;
    (c) cooling thereafter the resulting solution to a temperature ranging from about 0° C. to 5° C. thereby crystallizing the egg white lysozyme; and
    (d) then separating the thus crystallized egg white lysozyme from the solution.

2. The process of claim 1 wherein the salt solution is an aqueous solution of a salt selected from the group consisting of sodium, potassium and ammonium salts; the concentration of salt in said salt solution being of the order of 3 to 5% by weight.

3. The process of claim 1 wherein the salt solution is a buffer solution obtained by admixing a salt selected from the group consisting of sodium, potassium and ammonium salts with an aqueous solution of an acid having an anion constituting the salt; the concentration of salt in said salt solution being of the order of 3 to 5% by weight.

4. The process of claim 1 wherein the salt solution is a buffer solution obtained by admixing a salt selected from the group consisting of sodium, potassium and ammonium salts, with an aqueous solution of an alkali having a cation constituting the salt; the concentration of salt in said salt solution being of the order of 3 to 5% by weight.

5. The process of claim 1 wherein the salt solution comprising egg white lysozyme dissolved therein is an aqueous sodium chloride solution comprising crude egg white lysozyme dissolved therein.

6. The process of claim 1 wherein the salt solution having egg white lysozyme dissolved therein is a salt eluate obtained by eluting egg white lysozyme adsorbed on a weakly acidic cation exchange resin.

7. The process of claim 1 wherein the pH of the salt solution having egg white lysozyme dissolved therein has been adjusted to about 9.5, with 0.5 to 1.0N caustic soda, prior to the addition of the seed crystal of crystalline lysozyme.

8. The process of claim 1 wherein the seed crystal of crystalline lysozyme is added to the salt solution having egg white lysozyme dissolved therein in a proportion of about 3 to 50 mg as crystalline lysozyme per liter of the salt solution.

9. The process according to claim 1 wherein the salt solution is continually stirred at a speed of about 5 to 20 r.p.m. throughout the process.

* * * * *